US012700507B2

(12) United States Patent
Ray et al.

(10) Patent No.: US 12,700,507 B2
(45) Date of Patent: Aug. 4, 2026

(54) BODY SURFACE AREA CHART AND METHOD

(71) Applicant: The Research Institute at Nationwide Children's Hospital, Columbus, OH (US)

(72) Inventors: William Ray, Columbus, OH (US); Renata Fabia, Columbus, OH (US); R. Wolfgang Rumpf, Columbus, OH (US); Adrian Rajab, Columbus, OH (US)

(73) Assignee: The Research Institute of Nationwide Children's Hospital, Columbus, OH (US)

( * ) Notice: Subject to any disclaimer, the term of this patent is extended or adjusted under 35 U.S.C. 154(b) by 469 days.

(21) Appl. No.: 18/012,011

(22) PCT Filed: Jul. 1, 2021

(86) PCT No.: PCT/US2021/040148
§ 371 (c)(1),
(2) Date: Dec. 21, 2022

(87) PCT Pub. No.: WO2022/006434
PCT Pub. Date: Jan. 6, 2022

(65) Prior Publication Data
US 2023/0268074 A1 Aug. 24, 2023

Related U.S. Application Data

(60) Provisional application No. 63/046,776, filed on Jul. 1, 2020.

(51) Int. Cl.
*G16H 50/30* (2018.01)
*G16H 50/50* (2018.01)

(52) U.S. Cl.
CPC ............. *G16H 50/30* (2018.01); *G16H 50/50* (2018.01)

(58) Field of Classification Search
None
See application file for complete search history.

(56) References Cited

U.S. PATENT DOCUMENTS

2010/0172567 A1    7/2010    Prokoski
2011/0205052 A1*   8/2011    Clawson ................ A61B 5/747
                                                        340/539.12

(Continued)

OTHER PUBLICATIONS

Prieto et al. ("A system for 3D representation of burns and calculation of burnt skin area." Burns 37.7 (2011): 1233-1240) (Year: 2011).*

(Continued)

*Primary Examiner* — Christopher B Tokarczyk
(74) *Attorney, Agent, or Firm* — Watts Law, LLC; Samantha R. Smart

(57) ABSTRACT

A burn assessment chart, method of generation, and system is provided. The chart includes a front profile and a rear profile corresponding to front and rear human profiles, including a head, two arms and two legs. The chart includes longitudinal lines and lateral lines that intersect within either the front or rear profile to form segments that correspond to a percentage of a human's surface area (e.g., 1%, 0.5%, etc.). The segments can be marked at locations that correspond to burn indicators on a patient, and the marked segments counted to easily determine a total percentage of surface area of a human that is burned.

18 Claims, 10 Drawing Sheets

600

602 — DRAFTING FIRST PROFILE OF HUMAN BEING

604 — RENDERING PLURALITY OF SUBSTANTIALLY LONGITUDINAL LINES WITHIN FIRST PROFILE

606 — RENDERING SUBSTANTIALLY LATERAL LINES ACROSS SUBSTANTIALLY LONGITUDINAL LINES WITHIN FIRST PROFILE TO GENERATE PLURALITY OF SEGMENTS TO CORRESPOND TO PERCENTAGE OF SURFACE AREA OF HUMAN BEING

608 — DRAFT SECOND PROFILE OF HUMAN BEING

610 — RENDERING PLURALITY OF SUBSTANTIALLY LATERAL LINES WITHIN SECOND PROFILE

612 — RENDERING SUBSTANTIALLY LATERAL LINES ACROSS SUBSTANTIALLY LONGITUDINAL LINES WITHIN SECOND PROFILE TO GENERATE PLURALITY OF SEGMENTS TO CORRESPOND TO PERCENTAGE OF SURFACE AREA OF HUMAN BEING

(56)                    References Cited

U.S. PATENT DOCUMENTS

2014/0213910 A1*   7/2014   Durkin ................. A61B 5/0075
                                                              600/477
2017/0367580 A1*   12/2017   DiMaio ................. A61B 5/445

OTHER PUBLICATIONS

Rumpf et al. Entitled "Comparison of the Lund and Browder table to computed tomography scan three-dimensional surface area measurement for a pediatric cohort", Jan. 2018; URL:https://reader. elsevier.com/reader/sd/pii/S0022480417305358?token=17CD3EF5 7452ABA411D2989A5B0D00919A849B566A6B73F54687940ED 33A08268916E5CBA466F9DF1F51350BF24383DB&originRegi on+us-east-1&originCreation=20210901202500. Retrieved from online on Sep. 1, 2021; entire document.

International Preliminary Report on Patentability and Written Opinion of the International Searching Authority from priority application No. PCT/US2021/040148, filed Jul. 1, 2021. (13 pages).
International Search Report from priority application No. PCT/ US2021/040148, filed Jul. 1, 2021. (2 pages).
Extended European Search Report in corresponding European application No. 21831752.7 issued Jul. 5, 2024. (8 pages).
Ahn, Chris B. et al. Improving accuracy of burn referrals through the use of an internet-based burns chart. Eur J Plast Surg; published Oct. 9, 2010; vol. 34, No. 5; pp. 331-335. (5 pages).
Fontaine, Mathieu et al. The e-burn application—A simple mobile tool to assess TBSA of burn wounds. Science Direct; Feb. 2018, vol. 44, issue 1; pp. 237-238. (4 pages).
European Search Report and Written Opinion dated Oct. 23, 2025, in corresponding European Application No. 21 831 725.7-1113. (9 pages).

* cited by examiner

| LUND AND BROWDER CHART | % |
|---|---|
| HEAD | |
| NECK | |
| ANTERIOR TRUNK | |
| POSTERIOR TRUNK | |
| BUTTOCKS (RIGHT AND LEFT) | |
| GENITALIA | |
| UPPER RIGHT ARM | |
| UPPER LEFT ARM | |
| LOWER RIGHT ARM | |
| LOWER LEFT ARM | |
| RIGHT HAND | |
| LEFT HAND | |
| RIGHT THIGH | |
| LEFT THIGH | |
| RIGHT LEG | |
| LEFT LEG | |
| RIGHT FOOT | |
| LEFT FOOT | |
| TOTAL | |

FRONT    BACK

AGE: 5-9

INITIALS: _____

DEPARTMENT: _____

800

819    818  812    814

845

PROCESSING DEVICE 817    815

816

SECONDARY DEVICE

818

813

847

818

849

BODY SURFACE AREA CHART AND METHOD

CROSS REFERENCE TO RELATED APPLICATIONS

The following is a U.S. National phase patent application filed under 35 U.S.C. § 371 claiming priority to international patent application serial number PCT/US21/40148 having a filing date of Jul. 1, 2021 and was published by the International Bureau as publication number WO 2022/006434 on Jan. 6, 2022 which claims priority to U.S. Provisional Patent Application Ser. No. 63/046,776 filed Jul. 1, 2020 entitled BODY SURFACE AREA CHART AND METHOD. The entire contents of the above-identified application are incorporated herein by reference in their entireties for all purposes.

FIELD OF THIS DISCLOSURE

The present disclosure relates to a body surface area chart and method. More specifically, the present disclosure relates to a body surface area chart and method of use for improving identification of a body area surface that is burned for identifying proper treatment.

BACKGROUND

When utilizing traditional methods, determining burn surface area of a patient is wildly inaccurate. The methods that are used are based upon or similar to the Lund and Browder chart illustrated in FIG. 1. Historically, the burn estimates vary significantly, which causes oftentimes life-threatening and expensive problems during fluid resuscitation and tissue replacement of burn patients.

Increasing the accuracy of burn assessments for burn patients can result in shorter hospital stays and fewer complications. Additionally, increasing the accuracy of burn assessments for burn patients will reduce cost as the use of donor tissue is expensive, and using the correct amount prevents waste.

The Lund and Browder chart, illustrated in FIG. 1, has been the standard for determining TBSA-B (Total Body Surface Area—Burn) for decades. The Lund and Browder chart divides the human body into regions and assigns percentage of TBSA (Total Body Surface Area) to each region. The Lund and Browder chart is then used by assessors (e.g., first responders and other medical professionals) to assess how much of a patient's body is burned. This measurement is important, since subsequent treatment (e.g. fluid resuscitation, donor tissue, etc.) is dependent on an accurate measure of how much surface area of the patient's body is affected by the burn. One downside of the Lund and Browder chart occurs when patients have individual-to-individual variations (for example, longer or shorter legs) that can cause significant deviations from the Lund and Browder predicted values. Another problem with traditional TBSA charts stems from frequent user math errors.

Patients with burns exceeding 15% TSBA typically need continuous fluid administration to treat the burn in question. Responsive to a patient receiving too much fluid in response to a burn that does not exceed 15% TSBA, the patient may experience edema, compartment syndrome, and rupture of the skin areas surrounding the burn, causing more damage and slowing the healing process. Responsive to a patient receiving too little fluid, the healing process again is impacted negatively and kidney or multiple organ failure may occur. Additionally, should skin grafts be deemed necessary, the amount of precious donor skin to be used is determined using the TBSA-B calculations. Accurate TBSA-B measurements are required to ensure the best outcome for the patient. In pediatric patients, children with burns exceeding 10% TSBA typically need to be transported to specialty burn centers. Absent accurate measurements, treatment can become complicated, more costly, and/or harmful to patients.

SUMMARY

One aspect of the present disclosure includes a burn assessment chart for determining a percentage of surface area burned on a burn patient and identifying treatment, the burn assessment chart comprising a first profile and a second profile comprising a head, two arms, a torso, and two legs. The front profile corresponds to a front profile of a human and has a plurality of longitudinal lines within the first profile, a plurality of lateral lines intersecting the plurality of longitudinal lines within the first profile, the plurality of lateral lines and intersecting plurality of longitudinal lines forming a plurality of segments, wherein each segment of the plurality of first segments corresponds to a percentage of a total surface area of the front profile of a human. The second profile corresponds to a rear profile of human and has a plurality of longitudinal lines within the second profile, and a plurality of lateral lines intersecting the plurality of longitudinal lines within the second profile. The plurality of lateral lines and intersecting plurality of longitudinal lines form a plurality of segments, wherein each segment of the plurality of second segments corresponds to a percentage of a total surface area of the second profile of a human, wherein the plurality of segments of the first and second profiles is equal to one hundred percent.

Another aspect of the present disclosure includes a method of generating a burn assessment chart for determining a percentage of surface area of a burn patient that has been burned to identify treatment, the method comprising, rendering a first profile comprising a head, two arms, a torso, and two legs corresponding to a front profile of a human, drafting a plurality of longitudinal lines within the first profile, drafting a plurality of lateral lines intersecting plurality of longitudinal lines within the first profile to form a plurality of segments, wherein each segment of the plurality of first segments corresponds to a percentage of a total surface area of the front profile of the human. The method also includes rendering a second profile comprising a head, two arms, a torso, and two legs corresponding to a rear profile of the human, drafting a plurality of longitudinal lines within the second profile, and drafting a plurality of lateral lines intersecting the plurality of longitudinal lines within the second profile to form a plurality of segments, wherein each segment of the plurality of second segments corresponds to a percentage of a total surface area of the second profile of a human, wherein the plurality of segments of the first and second profiles is equal to one hundred percent.

An additional aspect of the present disclosure includes a burn assessment system for determining a percentage of surface area burned on a burn patient and identifying treatment, the burn assessment system comprising a digital body surface area chart comprising a first and a second profile corresponding to a front and back profile of a human, a plurality of longitudinal and lateral lines intersecting to create a plurality of first and second segments wherein each of the first and second segments corresponds to a percentage of a total surface area of the front and back profile. The system also includes a processing device having a processor wherein the processing device is configured to generate output based on inputs received from a secondary device, and a display screen coupled to the processing device, the display screen projecting the body surface area chart.

BRIEF DESCRIPTION OF THE DRAWINGS

The present disclosure relates to a body surface area chart and method of use. More specifically, the present disclosure relates to a body surface area chart and method of use for improving determination of a burned body surface area for use in identifying proper treatment.

The foregoing and other features and advantages of the present disclosure will become apparent to one skilled in the art to which the present invention relates upon consideration of the following description of the invention with reference to the accompanying drawings, wherein like reference numerals refer to like parts unless described otherwise throughout the drawings and in which.

Figure 1:
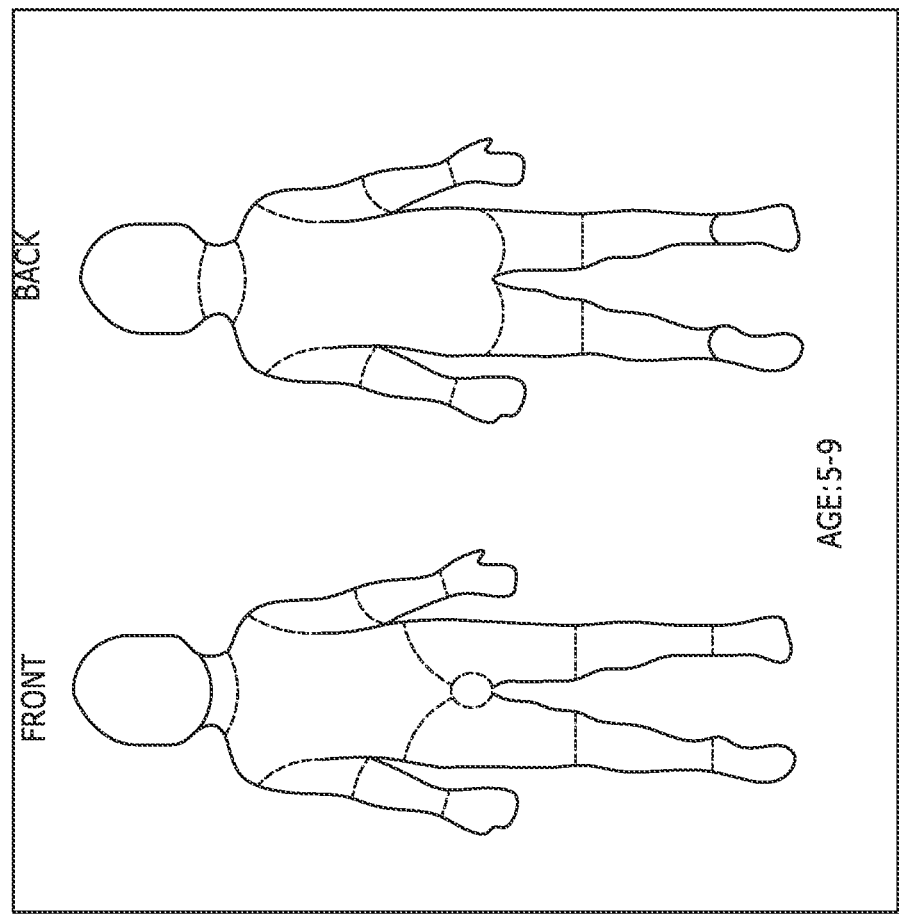
FIG. 1 is an illustration of a Lund and Browder Chart as known in the prior art.

Skilled artisans will appreciate that elements in the figures are illustrated for simplicity and clarity and have not necessarily been drawn to scale. For example, the dimensions of some of the elements in the figures may be exaggerated relative to other elements to help to improve understanding of embodiments of the present disclosure.

The apparatus and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein.

DETAILED DESCRIPTION

The present disclosure relates to a body surface area chart and method of use. More specifically, the present disclosure relates to a body surface area chart and method of use for improving identification of a body area surface that is burned in identifying proper treatment.

Figure 8:
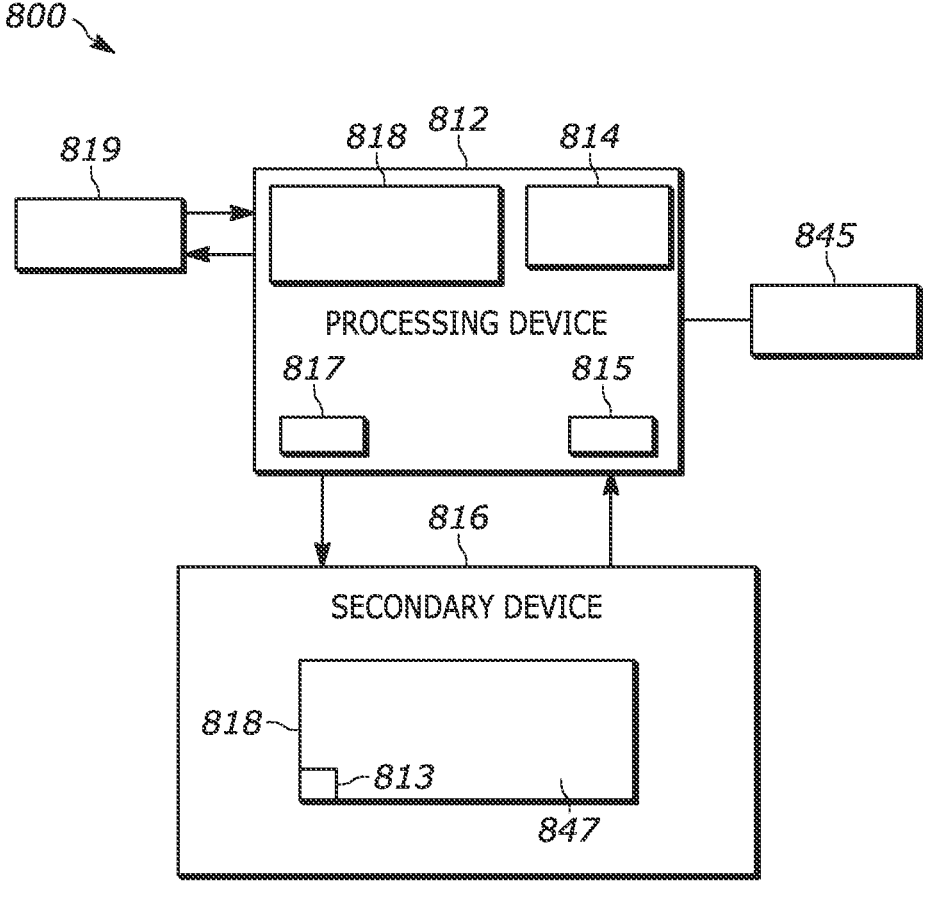
FIG. 8 is a schematic diagram of a body surface area chart system 800 for supporting an interactive surface area chart, in accordance with one example embodiment of the present disclosure.

FIG. 8 illustrates a schematic diagram of a body surface area chart system 800, in accordance with one of the exemplary embodiments of the disclosure. The body surface area chart system 800 includes a processing device 812, which includes a computing device (e.g. a database server, a file server, an application server, a computer, or the like) with computing capability and/or a processor 814. The processor 814 comprises a central processing unit (CPU), such as a programmable general purpose or special purpose microprocessor, and/or other similar device or a combination thereof.

The processing device 812 would generate outputs based upon inputs received from a secondary device 816, cloud storage, a local input from a user/assessor, etc. It would be appreciated by one having ordinary skill in the art that the processing device 812 would include a data storage device 817 in various forms of non-transitory, volatile, and non-volatile memories which would store buffered or permanent data as well as compiled programming codes 821 used to execute functions of the processing device 812. In another example embodiment, the data storage device 817 can be external to and accessible by the processing device 812, the data storage device 817 may comprise an external hard drive, cloud storage, and/or other external recording devices 819.

In one example embodiment, the processing device 812 comprises one of a remote or local computer system. The computer system includes desktop, laptop, tablet hand-held personal computing device, IAN, WAN, WWW, and the like, running on any number of known operating systems and is accessible for communication with remote data storage, such as a cloud, host operating computer, via a world-wide-web or Internet.

In another example embodiment, the processing device 812 comprises a processor, a data storage, computer system memory that includes random-access-memory ("RAM"), read-only-memory ("ROM") and/or an input/output interface. The processing device 812 executes instructions by non-transitory computer readable medium either internal or external to the processor that communicates to the processor via input interface and/or electrical communications, such as from the secondary device 816 (e.g., smart phone, tablet, personal computer, or other device). In yet another example embodiment, the processing device 812 communicates with the Internet, a network such as a LAN, WAN, and/or a cloud, input/output devices such as flash drives, remote devices such as a smart phone or tablet, and displays. In one example embodiment, the secondary device 816 includes a display 818, such as an interactive display, the display having visual, audio, etc. output, and/or touch screen capability. In another example embodiment, the processing device 812 includes a display 818a, the display having visual, audio, etc. output, and/or touch screen capability. In another example embodiment, the display 818, 818a, is a screen in contact with a keyboard or mouse that provides input to the processing device 812.

In one example embodiment, the body surface area chart system 800 is a web-based tool (e.g., no download or installation is needed to utilize the body surface area chart system 800). In another example embodiment, the body surface area chart system 800 is partially and/or completely downloadable to, for example, a processing device 812. The body surface area chart system 800 is interactive, meaning a user may change and alter their inputs in real-time.

Figures 2, 3:
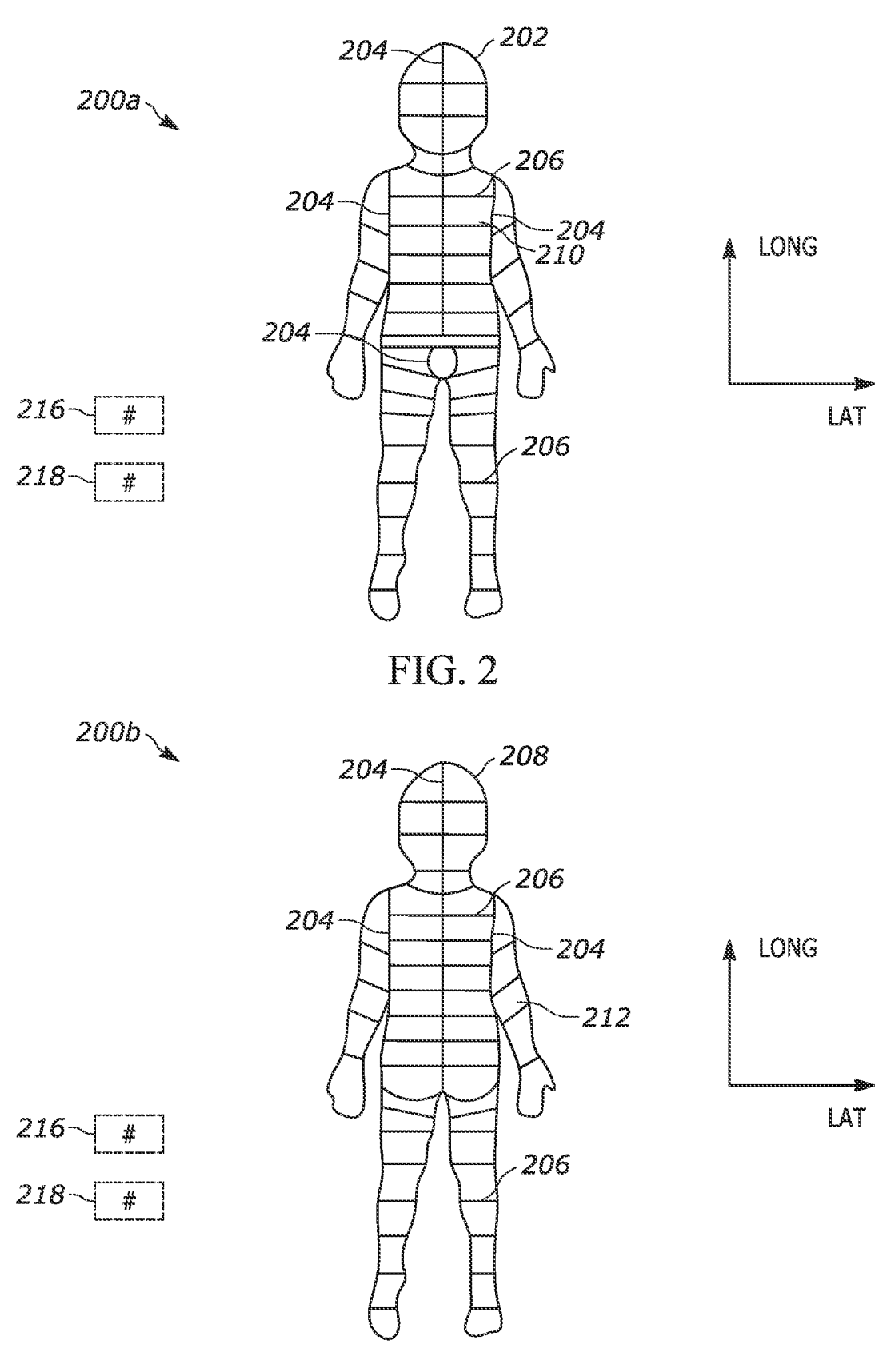
FIG. 2 is first profile view of a total body surface area chart that represents a human being for use in determining percent of a surface burn area relative to a total surface area of a burn patient, according to one embodiment of the present disclosure.
FIG. 3 is second profile view of a total body surface area chart that represents a human being for use in determining percent of a surface burn area relative to a total surface area of a burn patient, according to one embodiment of the present disclosure.

Illustrated in FIGS. 2-5 are body surface area charts 200, 300. The body surface charts 200, 300 minimize burn estimate errors through identification, organization, and standardization of the units of measure in the chart. In one example embodiment, FIGS. 2 and 3 are presented to the user on the display 818, 818a of the secondary device 816 or the processing device 812, respectively. In this example embodiment, the body surface area chart 200 is interactive.

In the example embodiment of FIG. 2, an outline 202 of a first profile 200a is illustrated. In one example embodiment, the first profile is a front profile 200a of a human (ranging from infant to adult) 813 having a plurality of substantially longitudinal section lines 204 extending along a longitudinal direction LONG and substantially lateral section lines 206 extending along a lateral direction LAT. In one example embodiment, the assessor, utilizing the display 818, 818a, selects an age, for example ranging from infant to adult, and the processing device 812 provides the front profile 200a corresponding to the selected age to the assessor. In one example embodiment, a longitudinal section line 204 is considered to extend along the longitudinal direction LONG wherein said line deviates between 45° to the right and 45° to the left of the LONG line.

In another example embodiment, the longitudinal section line 204 is considered to extend along the longitudinal direction LONG wherein an angle deviates at an angle transverse (other than normal) to the LAT line. In another example embodiment, a lateral section line 206 is considered to extend along the lateral direction LAT wherein an angle deviates at an angle transverse (other than normal) to the LONG line. In yet another example embodiment, the lateral section line 206 is considered to extend along the lateral direction LAT wherein the line deviates between 45° above and 45° below the LAT line. In the illustrated example embodiment, the plurality of longitudinal section lines 204 and the plurality of lateral section lines 206 generate a plurality of front segments 210 that correspond to a percentage of surface area of a human being.

In one example embodiment, the plurality of longitudinal section lines 204 and the plurality of lateral section lines 206 generate fifty (50) front segments 210. In one example embodiment, areas of the plurality of front segments 210 are variable, wherein one front segment may have a larger or smaller area than another front segment. In another example embodiment, areas of the plurality of front segments 210 are even.

In the example embodiment of FIG. 3, an outline 208 of a second profile 200b is illustrated. In one example embodiment, the second profile is a rear profile 200b of a human (ranging from infant to adult) having the plurality of substantially longitudinal section lines 204 extending along the longitudinal direction LONG and the plurality of substantially lateral section lines 206 extending along the lateral direction LAT. In another example embodiment, the assessor utilizing the display 818, 818a is presented with a corresponding rear profile based upon the age selected with regard to the front profile 200a. In yet another example embodiment, the assessor selects an age 813 of the patient, and the processing device 812 displays the rear profile 200b corresponding to the selected age to the assessor. In this example embodiment, the body surface area chart 200 is interactive, wherein the user is either presented with the front and rear view 200a, 200b simultaneously, or has the option to alternate between the two (e.g., such as by swiping, scrolling, etc., left and right or up and down).

The lateral and the longitudinal section lines 206, 204, respectively, are substantially the same as the lateral and the longitudinal section lines of the front profile 200a. In the illustrated example embodiment, the plurality of longitudinal section lines 204 and the plurality of lateral section lines 206 generate a plurality of rear segments 212 that correspond to a percentage of surface area of a human being. In one example embodiment, the plurality of longitudinal section lines 204 and the plurality of lateral section lines 206 generate fifty (50) rear segments 212.

In one example embodiment, areas of the plurality of rear segments 212 are variable, wherein one rear segment may have a larger or a smaller area than another rear segment. In another example embodiment, areas of the plurality of rear segments 212 are even. In yet another example embodiment, the human body is divided up evenly into many smaller segments of 1% (plurality of segments 210, 212). In another example embodiment, the human body is divided up into many variably sized smaller segments that correspond to about 1% of the human body.

Figures 4, 5:
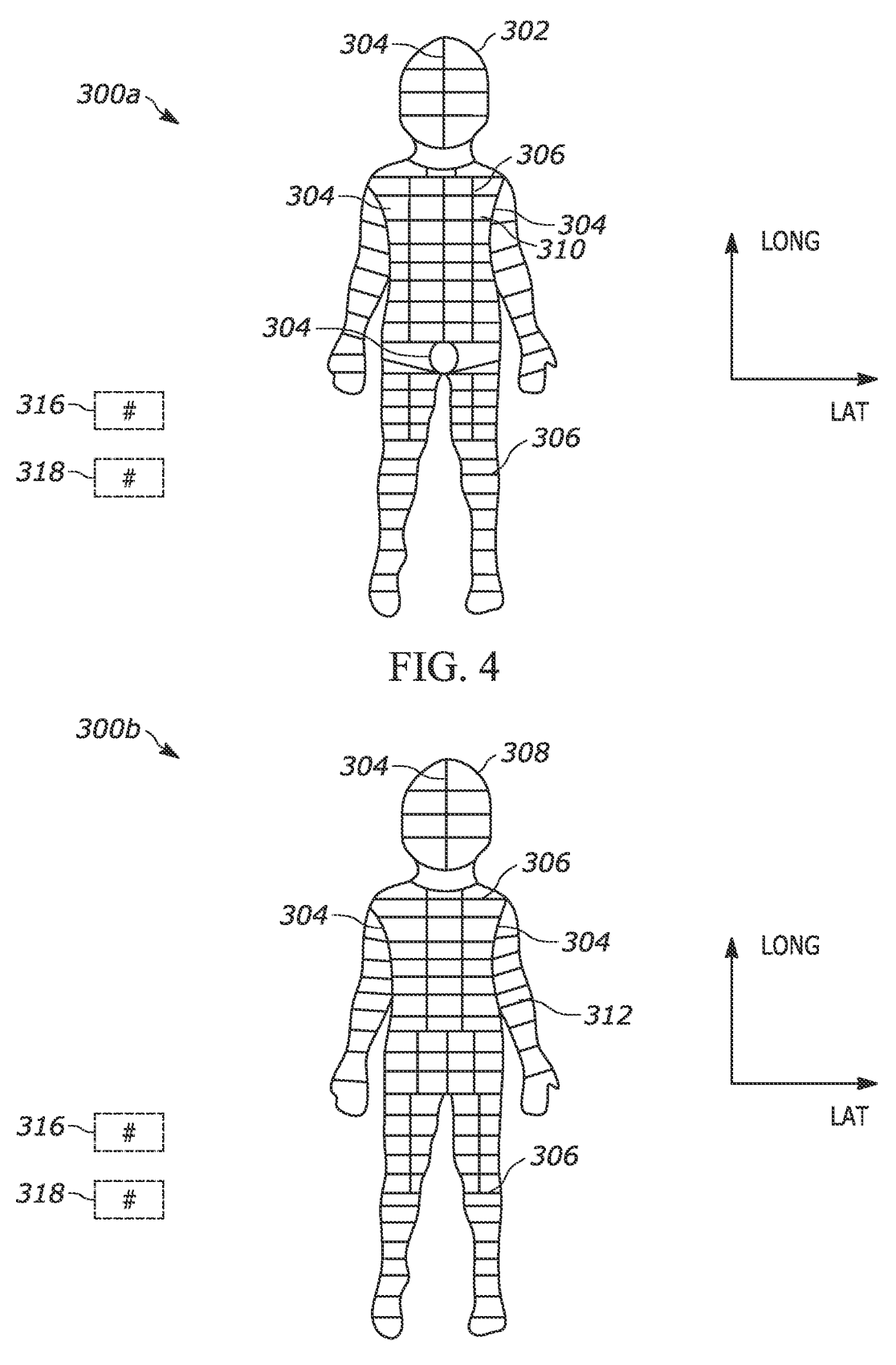
FIG. 4 is first profile view of a total body surface area chart that represents a human being for use in determining percent of a surface burn area relative to a total surface area of a burn patient, according to a second embodiment of the present disclosure.
FIG. 5 is second profile view of a total body surface area chart that represents a human being for use in determining percent of a surface burn area relative to a total surface area of a burn patient, according to a second embodiment of the present disclosure.

Referring now to FIGS. 4-5, another example embodiment of the body surface area chart 300 is shown. Features of the body surface area chart 300 illustrated in FIGS. 4-5 that are similar to the features of the body surface area chart 200 illustrated in FIGS. 2-3 will be identified by like numerals increased by a factor of one-hundred.

In the example embodiment of FIG. 4, an outline 302 of a front profile 300a of a human (ranging from infant to adult) having a plurality of substantially longitudinal section lines 304 extending along a longitudinal direction LONG and substantially lateral section lines 306 extending along a lateral direction LAT. In one example embodiment, the plurality of longitudinal section lines 304 and the plurality of lateral section lines 306 generate one hundred (100) front segments 310. In one example embodiment, areas of the plurality of front segments 310 are variable, wherein one front segment may have a larger or smaller area than another front segment. In another example embodiment, areas of the plurality of front segments 310 are even.

In the example embodiment of FIG. 5, an outline 308 of a rear profile 300b of a human (ranging from infant to adult) having the plurality of substantially longitudinal section lines 304 extending along the longitudinal direction LONG and the plurality of substantially lateral section lines 306 extending along the lateral direction LAT. In one example embodiment, the plurality of longitudinal section lines 304 and the plurality of lateral section lines 306 generate one hundred (100) rear segments 312. In one example embodiment, areas of the plurality of rear segments 312 are variable, wherein one rear segment may have a larger or smaller area than another rear segment. In another example embodiment, areas of the plurality of rear segments 312 are even. In this example embodiment, the human body is divided up at least one of evenly or variably into many smaller segments that correspond to about 0.5% of a surface area of a human (plurality of segments 310, 312).

In an example embodiment, wherein the processing device 812 is being utilized, the surface area chart 300 is presented in a same or similar manner on the display 818, 818a, as described above with regard to the surface area chart 200.

Figure 6:
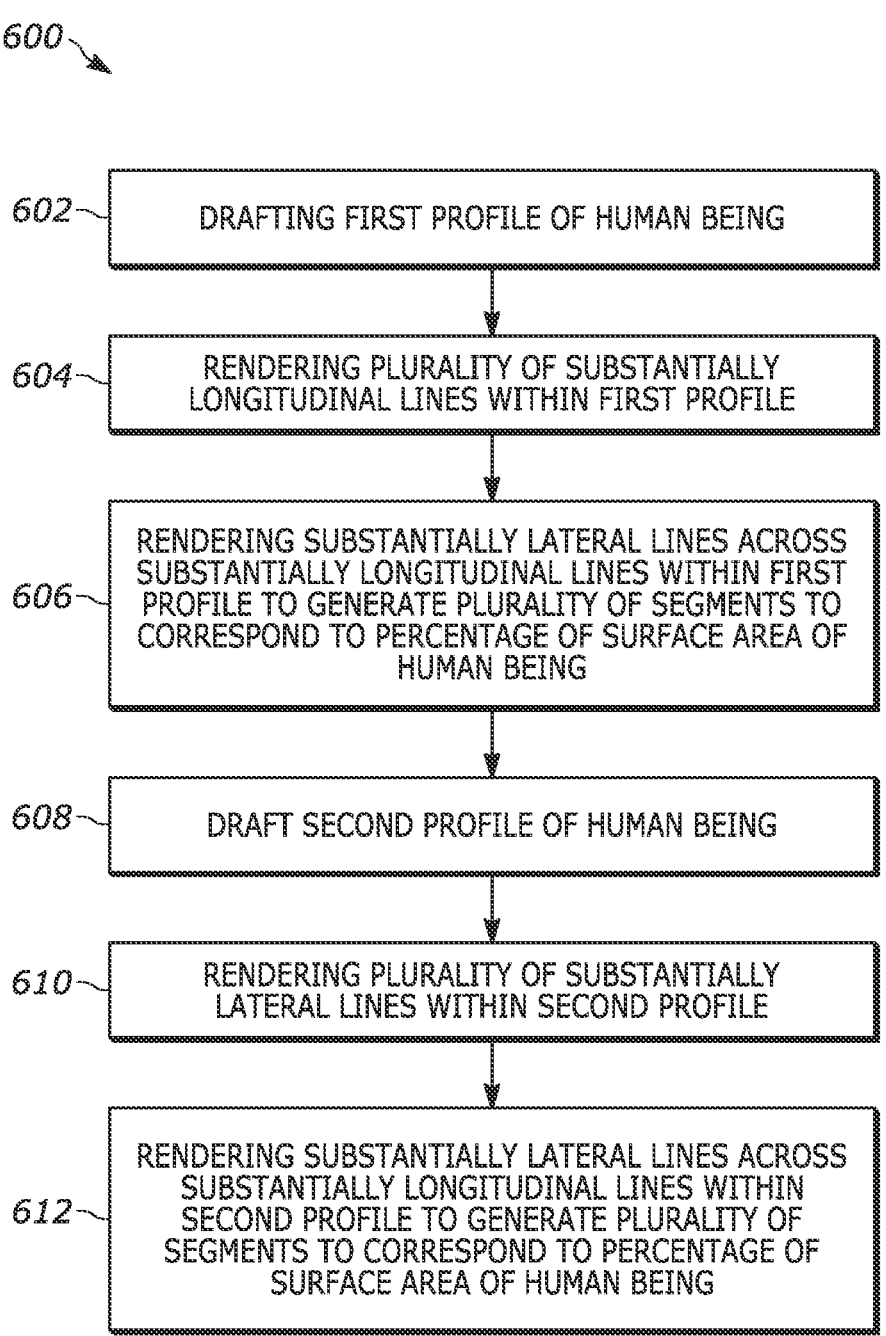
FIG. 6 is a schematic diagram of a method of making a total body surface area chart, according to one embodiment of the present disclosure.

In FIG. 6, a method 600 of generating the body surface area chart 200, 300 is illustrated. At 602, a first profile 200a, 300a of a human being is illustrated. The first profile comprises the front profile 200a, 300a. At 604, the plurality of substantially longitudinal lines 204, 304 are rendered within the first profile 200a, 300a. At 606, the plurality of substantially lateral lines 206, 306 are rendered across the plurality of substantially longitudinal lines 204, 304 to generate the plurality of segments 210, 310 that correspond to a percentage of the surface area of the human being. It would be appreciated that the lateral lines 204, 304 could be rendered after or concurrently with the longitudinal lines 206, 306. In one example embodiment, the plurality of longitudinal section lines 204 and the plurality of lateral section lines 206 are rendered to generate fifty (50) front segments 210. In another example embodiment, the plurality of longitudinal section lines 304 and the plurality of lateral section lines 306 are rendered to generate one hundred (100) front segments 310.

At 608, a second profile 200b, 300b of a human being is illustrated. The second profile comprises the rear profile 200b, 300b. At 610, the plurality of substantially longitudinal lines 204, 304 are rendered within the second profile 200b, 300b. At 612, the plurality of substantially lateral lines 206, 306 are rendered across the plurality of substantially longitudinal lines 204, 304 to generate the plurality of segments 210, 310 that correspond to a percentage of the surface area of the human being. It would be appreciated that the lateral lines 206, 306 could be rendered after or concurrently with the longitudinal lines 204, 304. In one example embodiment, the plurality of longitudinal section lines 204 and the plurality of lateral section lines 206 are rendered to generate fifty (50) rear segments 212. In another example embodiment, the plurality of longitudinal section lines 304 and the plurality of lateral section lines 306 are rendered to generate one hundred (100) rear segments 312. In yet another example embodiment, the number of segments 210, 212, 310, 312 is between 50 and 100. In one example embodiment, the first and second profiles 200a, 200b, 300a, 300b are presented on the display 818, 818a and the segments 210, 212, 310, 312 are filled in based upon user input 845, wherein the user enters or touches the segment and/or utilizes a secondary input 847 (e.g., mouse, keyboard, or the like) to illicit a visual indicator (e.g., color change, marking, etc.) illustrating that a segment of the segments 210, 212, 310, 312 has been selected.

Figure 7:
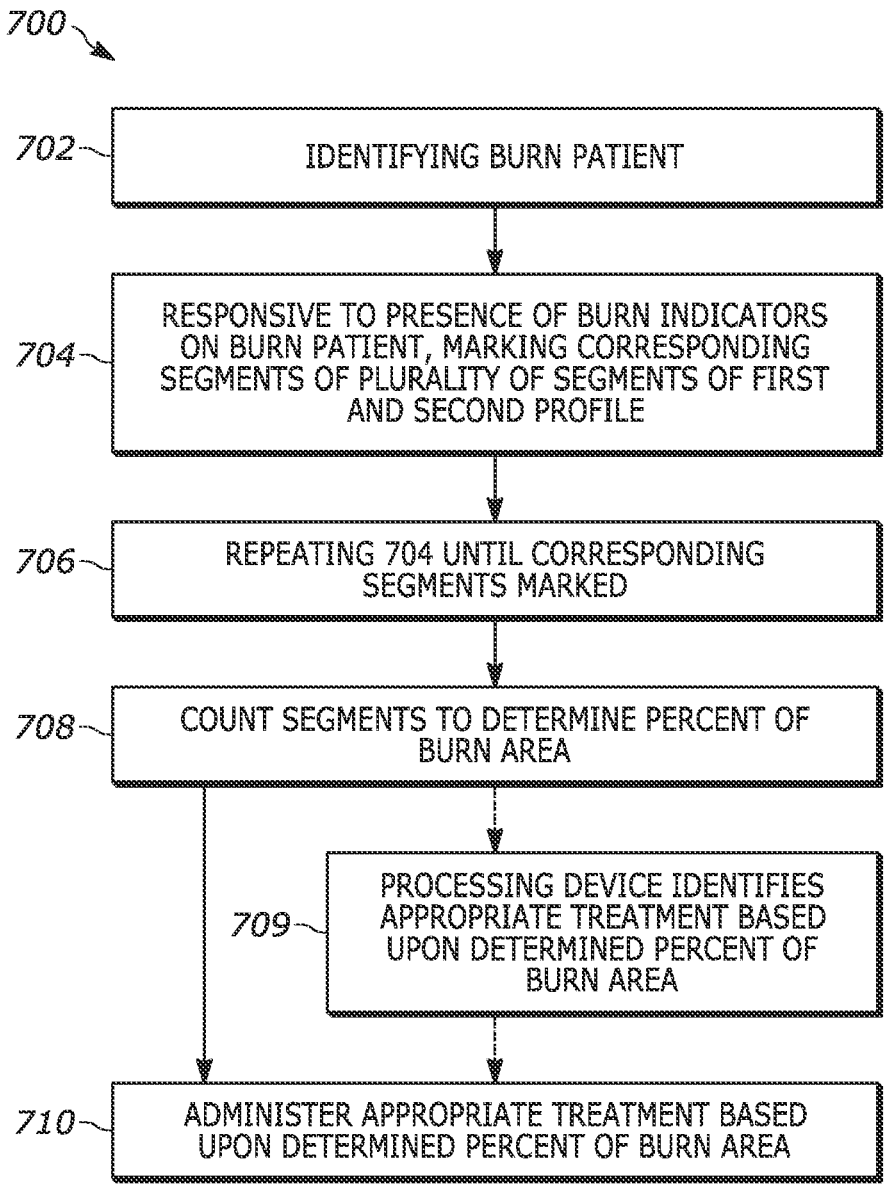
FIG. 7 is a schematic diagram of a method of using a total body surface area chart for burn treatment, according to one embodiment of the present disclosure.

In FIG. 7, a method 700 of using the body surface area chart 200, 300 is illustrated. At 702, an assessor and/or multiple assessors (emergency medical technician, nurse, etc.) identifies a burn patient. At 704, responsive to the presence of burn indicators (e.g., discoloration, heat, etc.) on the burn patient, the assessor marks segments 210, 212, or 310, 312 on the first and second profile 200a, 200b, or 300a, 300b of the respective body surface area chart 200, or 300 that correspond to the location of the burn indicators. In one example embodiment, the user selects front and rear segments 210, 212 or 310, 312 on the first and second profile 200a, 200b, or 300a, 300b of the respective body surface area chart 200, or 300 that correspond to burn indicators on the burn patient through interaction with the display 818, 818a, and/or elements that provide input 845, 847 to the display.

Figure 9:
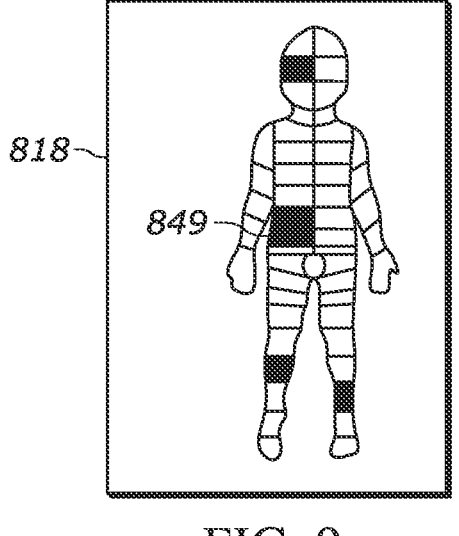
FIG. 9 is a digital body surface area chart featuring a display with burn indicators selected in accordance with one example embodiment of the present disclosure.

In one illustrated example embodiment shown in FIG. 9, the body surface area chart 200, or 300 on the display 818, 818a, provides the visual indicator that the segment 210, 212, 310, 312 has been selected. In another embodiment, the visual indicator that the segment 210, 212, 310, 312 has been selected is removable or can be "un-selected" through a second selection of the respective segment 210, 212, 310, 312, and/or a selection of a removal option. The segments selected by the assessor can be achieved by capacitive sensing on the display 818, human touch, stylus pen, or the like.

At 706, method step 704 is repeated until all segments 210, 212, 310, 312 corresponding to the burn indicators 849 are marked. In one example embodiment, the processing device 812 will display 818, 818a warnings, reminders, and/or pictures (e.g., pictures of second- or third-degree burns compared to first-degree burns) to remind assessors not to mark areas that contain merely first-degree burns. At 708, a total number of segments 210, 212, 310, 312 marked are counted to determine the percent of surface area that is burned. The segments 210, 212, 310, 312 are one of manually counted, such as by an assessor, or are counted by the processing device 812.

In one example embodiment, the processing device 812 displays on the display 818, 818a a running tally 216, 316, 416, 516, 1016 of the number of segments 210, 212, 310, 312, 410, 412, 510, 512, 1010, 1012 selected (see, for example, FIGS. 2-4, 12-17). In another example embodiment, the processing device 812 displays on the display 818, 818a a calculated percentage of surface area burned 218, 318, 418, 518, 1018 based upon the number of segments 210, 212, 310, 312, 410, 412, 510, 512, 1010, 1012 selected (see, for example, FIGS. 2-4, 12-17). In one example embodiment, the running tally 216, 316, 416, 516, 1016 and/or the percentage of surface area burned 218, 318, 418, 518, 1018 are constantly updated based upon the user selection.

For example, if 12 segments are selected on the body surface area chart 200 (e.g., where each segment corresponds to 1% of the burn patient's surface area), then the percent of surface area that is burned is 12%. In another example, if 52 segments are selected on the body surface area chart 300 (e.g., where each segment corresponds to 0.5% of the burn patient's surface area), then the assessor and/or the processing device 812 takes the total number 52 and divides by 2, and determines that the percent of surface area that is burned is 26%.

At 709, responsive to the processing device 812 having received the selected segments, the processing device 812 (e.g., though utilization of a database 817, a stored table, etc.) identifies an appropriate treatment based upon the determined percent of surface area burned and displays the appropriate treatment on the display 818, 818a. The treatment could be for example, oral medication, intravenous medication, compressions, wet compressions, and the like, or any combination thereof. At 710, the assessor administers the appropriate treatment based upon the determined percent of surface area that is burned.

In this example embodiment, the human body being divided up evenly or variably into many smaller segments, allows the assessor to mark down the segments 210, 212, 310, 312 that correspond with the burn indicators and then simply count the number of segments involved, and/or multiply the segments counted by a single number. In another example embodiment, the assessor indicates the segments 210, 212, 310, 312 that correspond with the burn indicators and the processing device 812 calculates the percent surface area burned.

Figure 10:
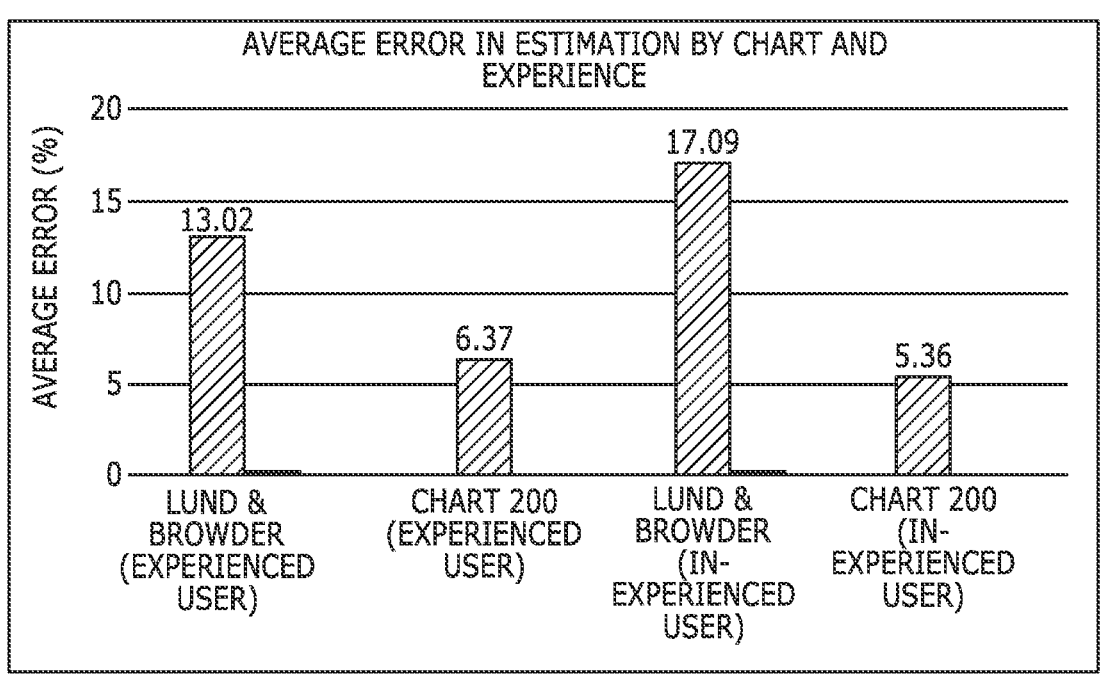
FIG. 10 is a chart illustrating the average error in determining a percentage of surface area determined to be burned by an experienced user using the Lund and Browder body chart (Lund & Browder), wherein experienced means a person having training in determining percentages of burned area on a patient, by an experienced user using the body surface area chart 200 (Chart 200), by an inexperienced user using the body surface area chart 200 (Chart 200), and by an inexperienced user using the Lund and Browder body chart (Lund & Browder), respectively.
Figure 11:
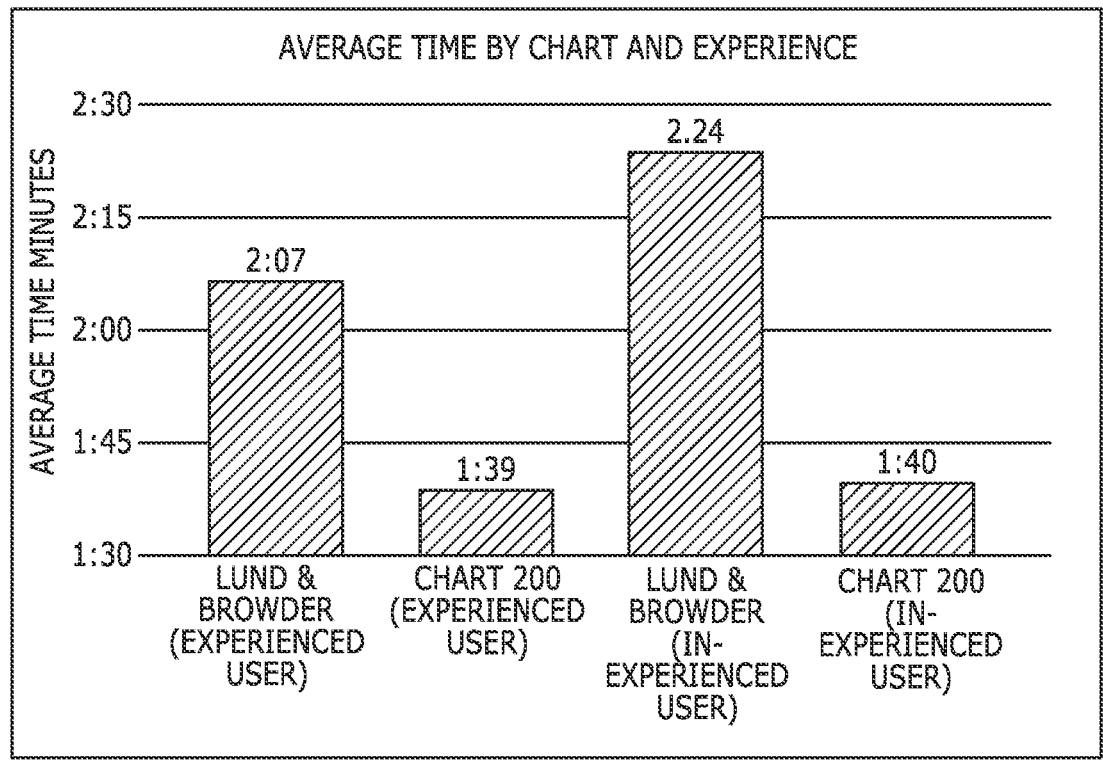
FIG. 11 is a chart illustrating the average time in minutes needed to determine a percentage of surface area burned by an experienced user using the Lund and Browder body chart (Lund & Browder), by an experienced user using the body surface area chart 200 (Chart 200), by an inexperienced user using the body surface area chart 200 (Chart 200), and, by an inexperienced user using the Lund and Browder body chart (Lund & Browder) respectively.

As indicated by FIGS. 10 and 11, the body surface area chart 200 was more accurate than the Lund and Browder chart when used by test assessors and laymen and did decreased a duration of assessment (e.g., marking the segments 210, 212).

FIG. 10 illustrates the average error in determining a percentage of surface area determined to be burned by an experienced user using the Lund and Browder body chart (Lund & Browder), wherein experienced means a person having training in determining percentages of burned area on a patient, by an experienced user using the body surface area chart 200 (Chart 200), by an inexperienced user using the body surface area chart 200 (Chart 200), and by an inexperienced user using the Lund and Browder body chart (Lund & Browder) respectively.

FIG. 10 also illustrates that the body surface area chart 200 is more accurate regardless of the experience of the users, as it is more accurate with both experienced and inexperienced users than the Lund and Browder chart is with experienced users. Chart 200 is also much more accurate when used by inexperienced users, compared to any users of the Lund and Browder chart.

FIG. 11 illustrates the average time in minutes needed to determine a percentage of surface area burned by an experienced user using the Lund and Browder body chart (Lund & Browder), by an experienced user using the body surface area chart 200 (Chart 200), by an inexperienced user using the body surface area chart 200 (Chart 200), and, by an inexperienced user using the Lund and Browder body chart (Lund & Browder) respectively. FIG. 11 illustrates that users, both experienced and inexperienced, using the body surface area chart 200 determined the percentage of surface area burned much faster than experienced users using the Lund & Browder chart. Further, inexperienced users using the body surface area chart 200 determined the percentage of surface area burned on average about 27 seconds faster than experienced users, and 44 seconds faster than inexperienced users.

FIGS. 10 and 11 illustrate that the body surface area chart 200 was the most efficient chart due to the minimal time taken and most accurate percentage. The original Lund and Browder chart is illustrated in FIGS. 10 and 11 to be the least efficient as it is inaccurate and time consuming.

Figure 12:
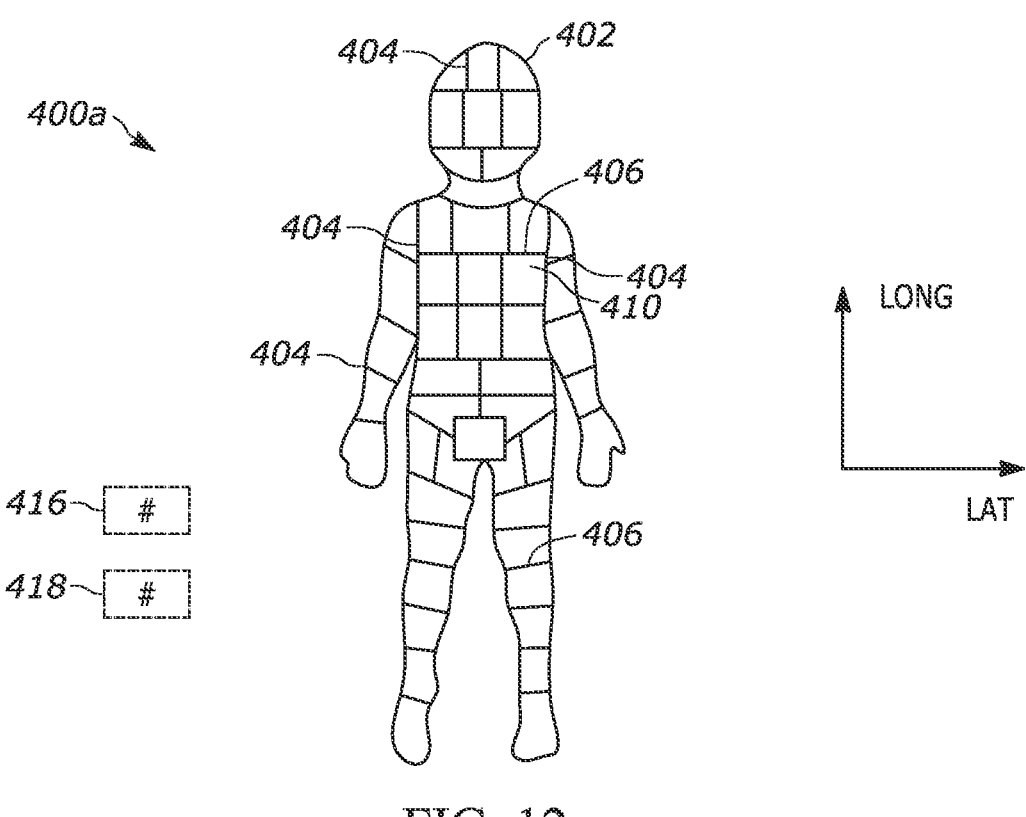
FIG. 12 is first profile view of a total body surface area chart that represents a human being for use in determining percent of a surface burn area relative to a total surface area of a burn patient ranging from ages 1-4 years, according to one embodiment of the present disclosure.
Figure 13:
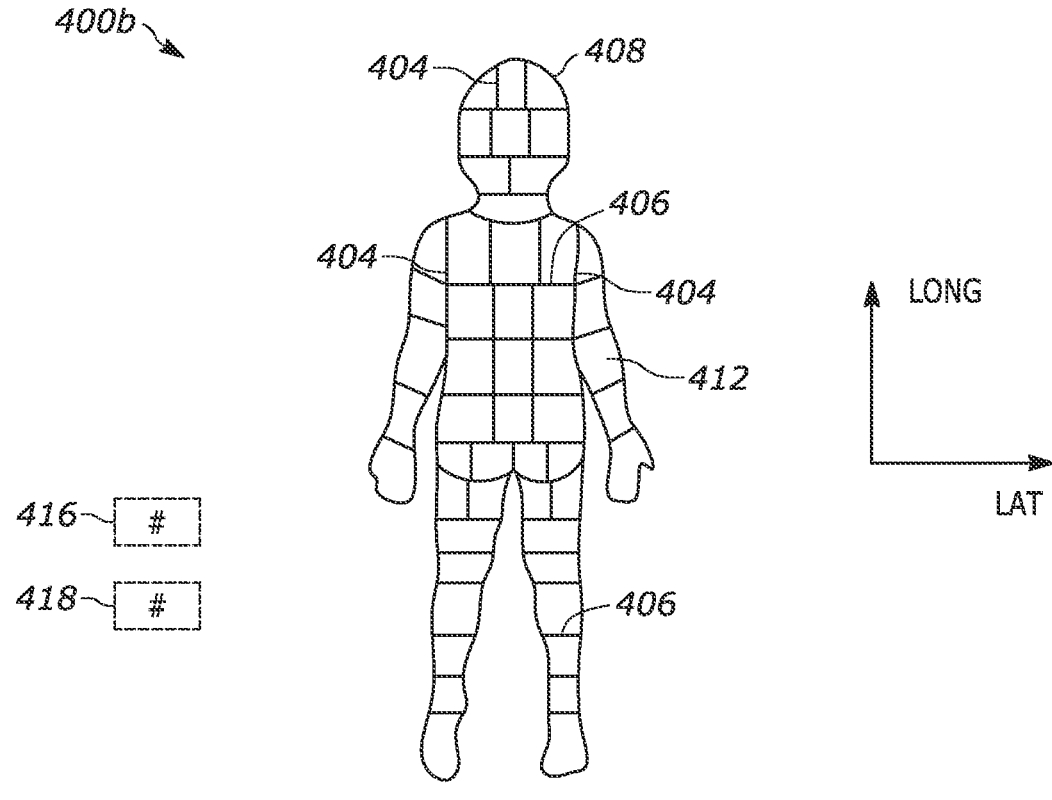
FIG. 13 is second profile view of a total body surface area chart that represents a human being for use in determining percent of a surface burn area relative to a total surface area of a burn patient ranging from ages 1-4 years, according to one embodiment of the present disclosure.

Referring now to FIGS. 12-13, a burn chart 400 designed for pediatric patients ranging from one through four years old is illustrated. One of many benefits of the burn chart 400 includes more conveniently placed anatomic segments (410, 412) in regard to the age range in question. Features of the body surface area chart 400 illustrated in FIGS. 12-13 that are similar to the features of the body surface area chart 300 illustrated in FIGS. 4-5 will be identified by like numerals increased by a factor of one-hundred.

In the example embodiment of FIG. 12, an outline 402 of a front profile 400a of a human (optimized for a human ranging from one through four years old) having a plurality of substantially longitudinal section lines 404 extending along a longitudinal direction LONG and substantially lateral section lines 406 extending along a lateral direction LAT. In one example embodiment, the plurality of longitudinal section lines 404 and the plurality of lateral section lines 406 generate forty-nine (49) front segments 410. In one example embodiment, areas of the plurality of front segments 410 are variable, wherein one front segment may have a larger or smaller area than another front segment. In another example embodiment, areas of the plurality of front segments 410 are even. An embodiment in which the plurality of front segments 410 comprises one hundred (100) segments and/or one half of one percent (0.5%) is also possible.

In the example embodiment of FIG. 13, an outline 408 of a rear profile 400b of a human (optimized for a human ranging from ages one through four years old) having the plurality of substantially longitudinal section lines 404 extending along the longitudinal direction LONG and the plurality of substantially lateral section lines 406 extending along the lateral direction LAT. In one example embodiment, the plurality of longitudinal section lines 404 and the plurality of lateral section lines 406 generate fifty-one (51) rear segments 412. In one example embodiment, areas of the plurality of rear segments 412 are variable, wherein one rear segment may have a larger or smaller area than another rear segment. In another example embodiment, areas of the plurality of rear segments 412 are even. In this example embodiment, the human body is divided up at least one of evenly or variably into many smaller segments that correspond to about 0.5% of a surface area of a human (plurality of segments 410, 412).

Figure 14:
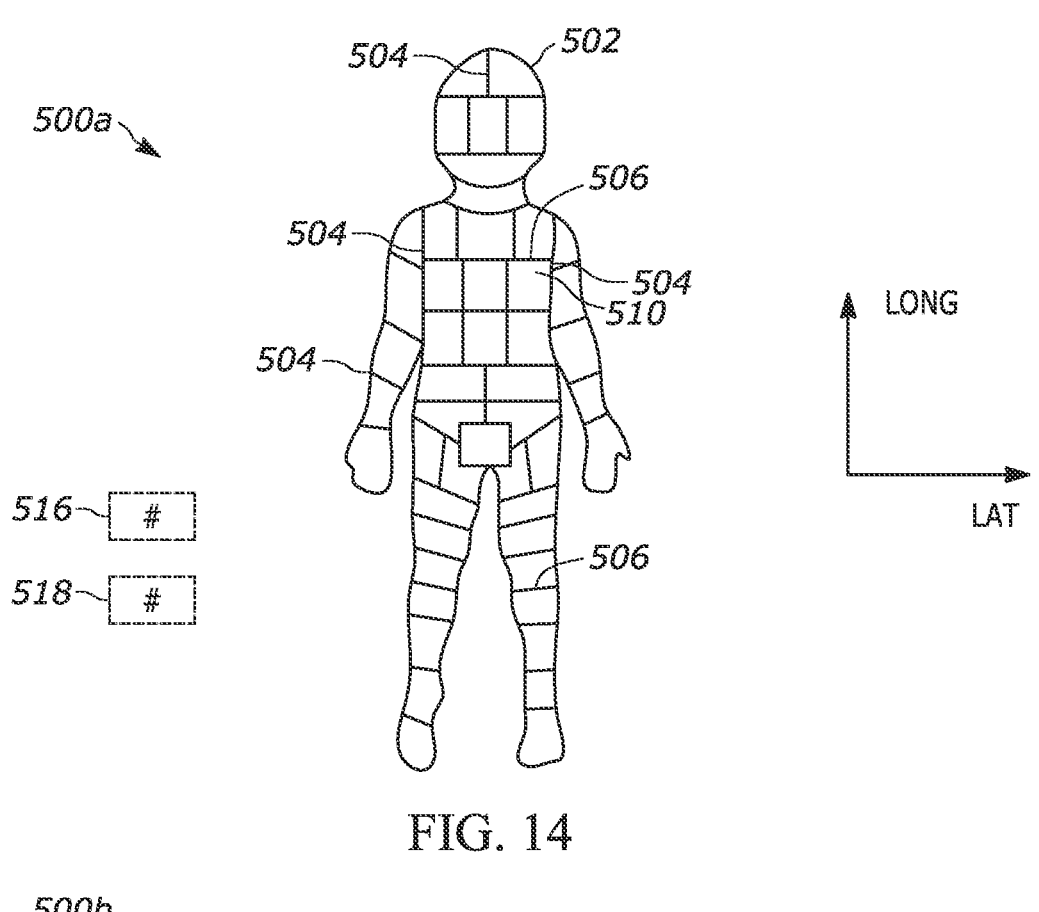
FIG. 14 is first profile view of a total body surface area chart that represents a human being for use in determining percent of a surface burn area relative to a total surface area of a burn patient ranging from ages 5-9 years, according to one embodiment of the present disclosure.
Figure 15:
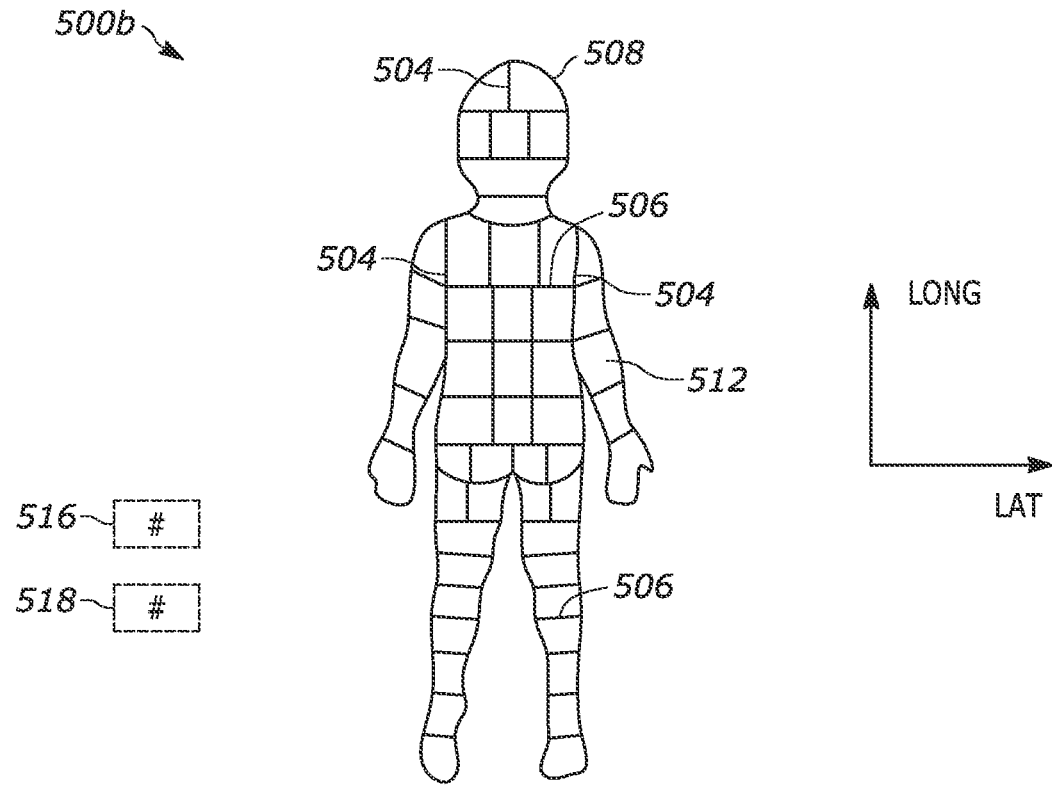
FIG. 15 is second profile view of a total body surface area chart that represents a human being for use in determining percent of a surface burn area relative to a total surface area of a burn patient ranging from ages 5-9 years, according to one embodiment of the present disclosure.

Referring now to FIGS. 14-15, a burn chart 500 designed for pediatric patients ranging from five through nine years old is illustrated. One of many benefits of the burn chart 500 includes more conveniently placed anatomic segments (510, 512) in regard to the age range in question. Features of the body surface area chart 500 illustrated in FIGS. 14-15 that are similar to the features of the body surface area chart 400 illustrated in FIGS. 12-13 will be identified by like numerals increased by a factor of one hundred.

In the example embodiment of FIG. 14, an outline 502 of a front profile 500a of a human (optimized for a human ranging from five through nine years old) having a plurality of substantially longitudinal section lines 504 extending along a longitudinal direction LONG and substantially lateral section lines 506 extending along a lateral direction LAT. In one example embodiment, the plurality of longitudinal section lines 504 and the plurality of lateral section lines 506 generate forty-nine (49) front segments 510. In one example embodiment, areas of the plurality of front segments 510 are variable, wherein one front segment may have a larger or smaller area than another front segment. In another example embodiment, areas of the plurality of front segments 510 are even. An embodiment in which the plurality of front segments 510 comprises one hundred (100) segments and/or one half of one percent (0.5%) is also possible.

In the example embodiment of FIG. 15, an outline 508 of a rear profile 500b of a human (optimized for a human ranging from ages five through nine years old) having the plurality of substantially longitudinal section lines 504 extending along the longitudinal direction LONG and the plurality of substantially lateral section lines 506 extending along the lateral direction LAT. In one example embodiment, the plurality of longitudinal section lines 504 and the plurality of lateral section lines 506 generate fifty-one (51) rear segments 512. In one example embodiment, areas of the plurality of rear segments 512 are variable, wherein one rear segment may have a larger or smaller area than another rear segment. In another example embodiment, areas of the plurality of rear segments 512 are even. In this example embodiment, the human body is divided up at least one of evenly or variably into many smaller segments that correspond to about 0.5% of a surface area of a human (plurality of segments 510, 512).

Figures 16, 17:
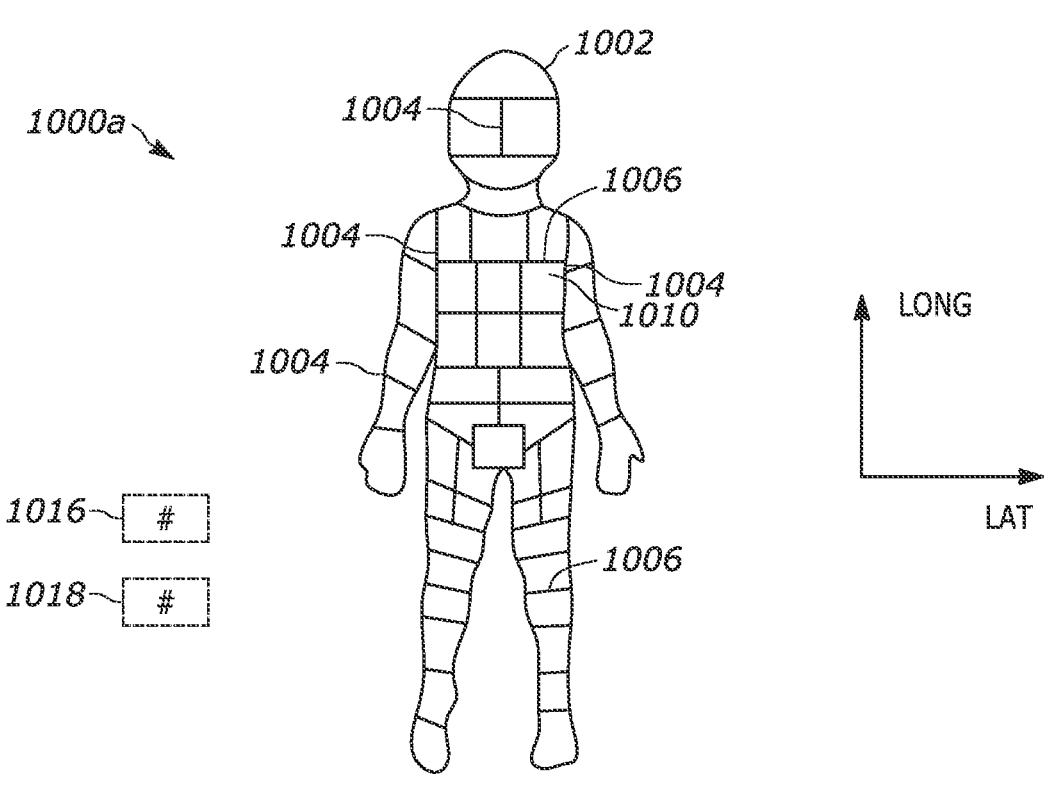
FIG. 16 is first profile view of a total body surface area chart that represents a human being for use in determining percent of a surface burn area relative to a total surface area of a burn patient ranging from ages 10-14 years, according to one embodiment of the present disclosure.
FIG. 17 is second profile view of a total body surface area chart that represents a human being for use in determining percent of a surface burn area relative to a total surface area of a burn patient ranging from ages 10-14 years, according to one embodiment of the present disclosure.

Referring now to FIGS. 16-17, a burn chart 1000 designed for pediatric patients ranging from ten through fourteen years old is illustrated. One of many benefits of the burn chart 1000 includes more conveniently placed anatomic segments (1010, 1012) in regard to the age range in question. Features of the body surface area chart 1000 illustrated in FIGS. 16-17 that are similar to the features of the body surface area chart 500 illustrated in FIGS. 14-15 will be identified by like numerals increased by a factor of five-hundred.

In the example embodiment of FIG. 16, an outline 1002 of a front profile 1000a of a human (optimized for a human ranging from ten through fourteen years old) having a plurality of substantially longitudinal section lines 1004 extending along a longitudinal direction LONG and substantially lateral section lines 1006 extending along a lateral direction LAT. In one example embodiment, the plurality of longitudinal section lines 1004 and the plurality of lateral section lines 1006 generate forty-nine (49) front segments 1010. In one example embodiment, areas of the plurality of front segments 1010 are variable, wherein one front segment may have a larger or smaller area than another front segment. In another example embodiment, areas of the plurality of front segments 1010 are even. An embodiment in which the plurality of front segments 1010 comprises one hundred (100) segments and/or one half of one percent (0.5%) is also possible.

In the example embodiment of FIG. 17, an outline 1008 of a rear profile 1000b of a human (optimized for a human ranging from ages ten through fourteen years old) having the plurality of substantially longitudinal section lines 1004 extending along the longitudinal direction LONG and the plurality of substantially lateral section lines 1006 extending along the lateral direction LAT. In one example embodiment, the plurality of longitudinal section lines 1004 and the plurality of lateral section lines 1006 generate fifty-one (51) rear segments 1012. In one example embodiment, areas of the plurality of rear segments 1012 are variable, wherein one rear segment may have a larger or smaller area than another rear segment. In another example embodiment, areas of the plurality of rear segments 1012 are even. In this example embodiment, the human body is divided up at least one of evenly or variably into many smaller segments that correspond to about 0.5% of a surface area of a human (plurality of segments 1010, 1012). In the foregoing specification, specific embodiments have been described. However, one of ordinary skill in the art appreciates that various modifications and changes can be made without departing from the scope of the disclosure as set forth in the claims below. Accordingly, the specification and figures are to be regarded in an illustrative rather than a restrictive sense, and all such modifications are intended to be included within the scope of present teachings.

The benefits, advantages, solutions to problems, and any element(s) that may cause any benefit, advantage, or solution to occur or become more pronounced are not to be construed as a critical, required, or essential features or elements of any or all the claims. The disclosure is defined solely by the appended claims including any amendments made during the pendency of this application and all equivalents of those claims as issued.

Moreover, in this document, relational terms such as first and second, top and bottom, and the like may be used solely to distinguish one entity or action from another entity or action without necessarily requiring or implying any actual such relationship or order between such entities or actions. The terms "comprises," "comprising," "has", "having," "includes", "including," "contains", "containing" or any other variation thereof, are intended to cover a non-exclusive inclusion, such that a process, method, article, or apparatus that comprises, has, includes, contains a list of elements does not include only those elements but may include other elements not expressly listed or inherent to such process, method, article, or apparatus. An element proceeded by "comprises . . . a", "has . . . a", "includes . . . a", "contains . . . a" does not, without more constraints, preclude the existence of additional identical elements in the process, method, article, or apparatus that comprises, has, includes, contains the element. The terms "a" and "an" are defined as one or more unless explicitly stated otherwise herein. The terms "substantially", "essentially", "approximately", "about" or any other version thereof, are defined as being close to as understood by one of ordinary skill in the art, and in one non-limiting embodiment the term is defined to be within 10%, in another embodiment within 5%, in another embodiment within 1% and in another embodiment within 0.5%. The term "coupled" as used herein is defined as connected or in contact, although not necessarily directly and not necessarily mechanically. A device or structure that is "configured" in a certain way is configured in at least that way, but may also be configured in ways that are not listed.

The Abstract of the Disclosure is provided to allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in various embodiments for the purpose of streamlining the disclosure. This method of disclosure is not to be interpreted as reflecting an intention that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separately claimed subject matter.

We claim:

1. A burn assessment chart for determining a percentage of surface area burned on a burn patient and identifying treatment for presentation on an interactive surface, the burn assessment chart comprising:
   a first profile comprising a head, two arms, a torso, and two legs corresponding to a front profile of human;
   a plurality of longitudinal lines within the first profile;
   a plurality of lateral lines intersecting the plurality of longitudinal lines within the first profile;
   the plurality of lateral lines and intersecting plurality of longitudinal lines forming a plurality of segments, wherein each segment of the plurality of first segments corresponds to a percentage of a total surface area of the front profile of a human;
   a second profile comprising a head, two arms, a torso, and two legs corresponding to a rear profile of human;
   a plurality of longitudinal lines within the second profile;
   a plurality of lateral lines intersecting the plurality of longitudinal lines within the second profile;
   the plurality of lateral lines and intersecting plurality of longitudinal lines forming a plurality of segments, wherein each segment of the plurality of second segments corresponds to a percentage of a total surface area of the second profile of a human, wherein the plurality of segments of the first and second profiles is equal to one hundred percent, and wherein the first and second segments have an equal surface area, further wherein each of the segments comprises one of one percent or two percent of the total surface area of the first and second profiles, wherein the first and second segments are selectable via contact with a particular segment of the first and second segments on the interactive surface.

2. The burn assessment chart of claim 1, the plurality of first segments comprising fifty segments having an equal surface area and the plurality of second segments comprising fifty segments having an equal surface area.

3. The burn assessment chart of claim 1, the plurality of first segments comprising one-hundred segments having an equal surface area and the plurality of second segments comprising one-hundred segments having an equal surface area.

4. The burn assessment chart of claim 1, the interactive surface is a screen of a tablet, smartphone, or laptop.

5. The burn assessment chart of claim 1, wherein the burn assessment chart is coupled to a web-based application generating a visual display, the visual display projecting the features of the burn assessment chart onto the interactive surface.

6. A method of generating a burn assessment chart for determining a percentage of surface area of a burn patient that has been burned to identify treatment, the method comprising:
   rendering a first profile comprising a head, two arms, a torso, and two legs corresponding to a front profile of human;
   drafting a plurality of longitudinal lines within the first profile;
   drafting a plurality of lateral lines intersecting the plurality of longitudinal lines within the first profile, to form a plurality of first segments, wherein each segment of the plurality of first segments correspond to a percentage of a total surface area of the front profile of a human;
   rendering a second profile comprising a head, two arms, a torso, and two legs corresponding to a rear profile of the human;
   drafting a plurality of longitudinal lines within the second profile; and
   drafting a plurality of lateral lines intersecting the plurality of longitudinal lines within the second profile, to form a plurality of second segments, wherein each segment of the plurality of second segments corresponds to a percentage of a total surface area of the second profile of the human, wherein the plurality of first and second segments of the first and second profiles is equal to one hundred percent, further wherein, each of the first and second segments correspond to one percent of the of the total surface area of the first and second profiles, the first and second segments being selectable by a user, the selection corresponding to an observed burn of a burn patient.

7. The method of generating a burn assessment chart of claim 6, wherein the plurality of first segments comprises fifty segments having an equal surface area and the plurality of second segments comprising fifty segments having an equal surface area.

8. The method of generating a burn assessment chart of claim 7, the plurality of first and second segments being selectable based upon an interaction with a specific segment of the plurality of first and second segments, wherein each segment selected corresponds to an observed burn.

9. The method of generating a burn assessment chart of claim 6, the plurality of first segments comprising one-hundred segments having a variable surface area and the plurality of second segments comprising one-hundred segments having a variable surface area.

10. The method of generating a burn assessment chart of claim 6 further comprising the steps of:
    providing a processing device having a processor comprising data storage and memory, wherein the processor is configured to generate output based on secondary input;
    providing a visual display, the visual display being coupled with the processor, the visual display projecting the features of the burn assessment chart;
    providing a visual indicator on the visual display responsive to selection of first and second segments selected by the secondary input;
    storing the first and second segments selected on the processing device; and
    tabulating the total number of first and second segments selected.

11. The method of generating a burn assessment chart of claim 10 further comprises the step of assigning a percentage of body surface area based upon the tabulation of a total number of first and second segments selected.

12. The method of generating a burn assessment chart of claim 10, wherein the secondary input comprises any one of a local input, a smart phone, a computer, a tablet, or a cloud storage.

13. A burn assessment system for determining a percentage of surface area burned on a burn patient and identifying treatment, the burn assessment system comprising:
   a digital body surface area chart comprising a first and a second profile corresponding to a front and back profile of a human, a plurality of longitudinal and lateral lines intersecting to create a plurality of first and second segments wherein each of the first and second segments corresponds to a percentage of a total surface area of the front and back profile, further wherein the first and second segments correspond to at one percent of the total surface area of the front and back profile;
   a processing device having a processor wherein the processing device is configured to generate output based on inputs received from a secondary device; and a display screen coupled to the processing device, the display screen comprising an interactive surface projecting the body surface area chart, wherein the interactive surface is configured to receive a plurality of segment selections corresponding to an observed burn area of the burn patient.

14. The burn assessment system of claim 13, wherein the secondary input comprises any one of a local input, a smart phone, a computer, a tablet, or a cloud storage.

15. The burn assessment system of claim 13, the plurality of first and second segments comprising one-hundred segments having an equal surface area.

16. The burn assessment system of claim 13, the plurality of first and second segments comprising one-hundred segments having a variable surface area.

17. The burn assessment system of claim 13, the plurality of first and second segments comprising two-hundred segments having an equal surface area.

18. The burn assessment system of claim 13, the plurality of first and second segments comprising two-hundred segments having a variable surface area.

* * * * *